United States Patent
Poisson et al.

(10) Patent No.: US 6,415,800 B2
(45) Date of Patent: *Jul. 9, 2002

(54) METHOD OF SHAVING AND A DISPENSING APPARATUS THEREFOR

(75) Inventors: Norman D. Poisson, Andover, MA (US); Arlene H. Solbeck, Gaithersburg; James L. Solan, Rockville, both of MD (US); Luz Seidensticker, Forest Hills, PA (US); John V. Lawler, North Potomac, MD (US); Kirsten D. Burgess-Agee, North Bethesda, MD (US); Richard H. Cohen, Boyds, MD (US)

(73) Assignee: The Gillette Company, Boston, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/483,162

(22) Filed: Jan. 14, 2000

(51) Int. Cl.[7] ............................... B26D 7/34
(52) U.S. Cl. .............................. 132/200; 83/22
(58) Field of Search .................. 132/200, 289; 83/22, 14

(56) References Cited

U.S. PATENT DOCUMENTS

| | | | |
|---|---|---|---|
| 3,777,597 A | * 12/1973 | Herb | .............. 83/22 |
| 3,956,951 A | * 5/1976 | Jennings, Sr. | .............. 83/14 |
| 4,013,595 A | 3/1977 | Podella et al. | |
| 4,082,223 A | 4/1978 | Nozawa | |
| 4,161,288 A | 7/1979 | McKinney | |
| 4,178,364 A | * 12/1979 | Rucker | .............. 83/22 |
| 4,350,298 A | 9/1982 | Tada | |
| 4,434,917 A | 3/1984 | Saito et al. | |
| 4,495,168 A | 1/1985 | Schmolka | |
| 4,495,169 A | 1/1985 | Schmolka | |
| 4,534,958 A | 8/1985 | Adams et al. | |
| 4,558,821 A | 12/1985 | Tada et al. | |
| 4,720,046 A | 1/1988 | Morane | |
| 4,974,319 A | 12/1990 | Maguire, Jr. et al. | |
| 5,018,543 A | 5/1991 | Martinez et al. | |
| 5,174,992 A | * 12/1992 | Lindauer et al. | .............. 83/14 |
| 5,431,345 A | 7/1995 | Lund et al. | |
| 5,602,091 A | 2/1997 | Monson et al. | |
| 5,759,531 A | 6/1998 | Devaine et al. | |
| 5,922,333 A | 7/1999 | Laughlin | |
| 6,004,920 A | 12/1999 | Pollack et al. | |
| 6,012,463 A | * 1/2000 | Mitchell, Jr. | .............. 132/200 |
| 6,093,386 A | 7/2000 | Sampino et al. | |

FOREIGN PATENT DOCUMENTS

| | | |
|---|---|---|
| FR | 2 345 996 | 3/1977 |
| FR | 2 631 876 | 12/1989 |
| GB | 1142090 | 2/1969 |
| WO | WO 96/11249 | 4/1996 |

OTHER PUBLICATIONS

Johnsen, *Spray Technology & Marketing*, Jun. 1999, 24–28, 40–42.
McKenna, *Aerosol Age*, Nov. 1970, 24–28.
Sciarra, *Aerosol Age*, Nov. 1970, 18–22.
Shepherd (editor), *Aerosols: Science and Technology*, Interscience Publishers, Inc., New York, 144–149.
Wilkinson and Moore (editors), *Harry's Cosmeticology*, Seventh Edition, Chemical Publishing, New York, 1982, 156–189.
Yuhas, *Aerosol Age*, Apr. 1970, 14–15.

* cited by examiner

*Primary Examiner*—Todd E. Manahan
(74) *Attorney, Agent, or Firm*—Fish & Richardson P.C.

(57) ABSTRACT

Disclosed is a method of shaving hair by spraying a shaving preparation directly onto an area of skin to form a dispersed layer of the shaving preparation without the need for hand spreading and shaving the area with a razor. Also disclosed is a dispensing apparatus for spraying a shaving preparation directly onto an area of skin to be shaved. The shaving preparation may be an aerosol or a non-aerosol shaving preparation.

30 Claims, 1 Drawing Sheet

METHOD OF SHAVING AND A DISPENSING APPARATUS THEREFOR

BACKGROUND OF THE INVENTION

This invention relates to a method of shaving and a dispensing apparatus for dispensing shaving preparations.

Shaving preparations are designed for application to skin to facilitate the removal of hair from the skin using a razor. The shaving preparation softens and supports the hair prior to cutting, and lubricates the passage of the razor over the skin. An extensive discussion regarding the formulation of various shaving preparations may be found in *Harry's Cosmeticology*, Seventh Edition, J. B. Wilkinson and R. J. Moore (editors), Chemical Publishing, New York, 1982, pp. 156–189.

Currently, the most widely used forms of shaving preparation are the types referred to as instant foams and self-foaming gels (also known as post-foaming gels). Instant foams comprise water, a dispersed or solubilized surface-active agent (e.g., an anionic, cationic, amphoteric, or non-ionic surface-active agent, or combination thereof), and a propellant/blowing agent. They may also include ingredients such as foam builders, foam stabilizers, emollients, viscosity modifiers, lubricants, humectants, preservatives, and fragrance. They are dispensed from pressurized aerosol containers in the form of a rich lather for spreading by hand on the area to be shaved, which preferably has been washed and left wet to help soften and prepare the hair further. Self-foaming gels include many of the same ingredients as instant foams, and must be worked into a lather upon application by hand to the area to be shaved.

Hand-applied shaving preparations are typically used in connection with removing hair from facial skin. However, hand-applied shaving preparations dispensed from an aerosol container in the form of gels, foams, and lotions also exist for removing hair from larger areas such as legs. Typically, the shaving preparation is dispensed first onto the user's hand and then applied by hand to the leg. However, the user may also apply a dollop of foam or a ribbon of gel directly on the leg, then spread it out by hand over the entire surface to be shaved. Because the shaving preparation must be spread by hand to distribute it over the surface to be shaved, the shaving process is messy and inconvenient. For example, a slippery shave preparation can prevent a shaver from maintaining a firm grip of the shaving article. In addition, the process requires repeated hand rinsing and, in general, is time consuming.

Another popular option in the case of legs involves the simple application by hand of soap, in the form of a bar or liquid, or body wash, along with water. This method is just as messy and inconvenient as the aforedescribed shaving preparations, but without the same level of shaving performance, skin benefits, and application aesthetics.

SUMMARY OF THE INVENTION

The invention embraces a method of shaving hair by spraying a shaving preparation directly onto an area of skin to form a dispersed layer of the shaving preparation without the need for hand spreading, and shaving the area with a razor. The invention also embraces a dispensing apparatus for spraying a shaving preparation directly onto an area of skin to be shaved. The dispensing apparatus may be a pump spray or aerosol device. Preferably the shaving preparation forms a lather or foam upon contact with the skin. Since the shaving preparation is applied directly to the area of skin to be shaved, this simplifies application and avoids the inconvenience and messiness associated with hand-applied preparations. The method and apparatus of the present invention are especially useful for applying the shaving preparation to large skin areas to be shaved, such as the legs, since the spray will quickly cover a wide area.

DETAILED DESCRIPTION

Figure 1:
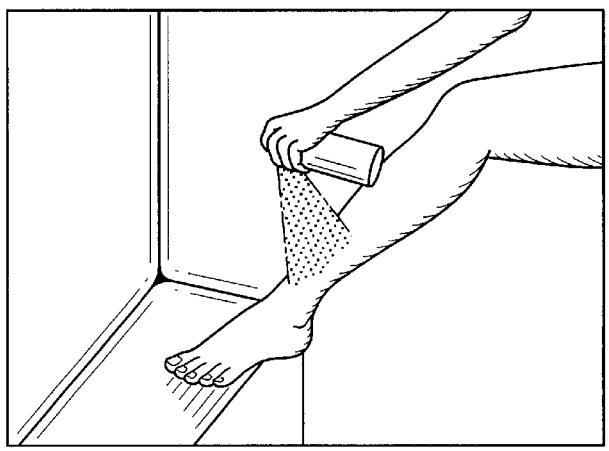
FIG. 1 illustrates a woman using a dispensing apparatus of the present invention to spray a shaving preparation directly onto her leg in accordance with the present invention.
Figure 1:
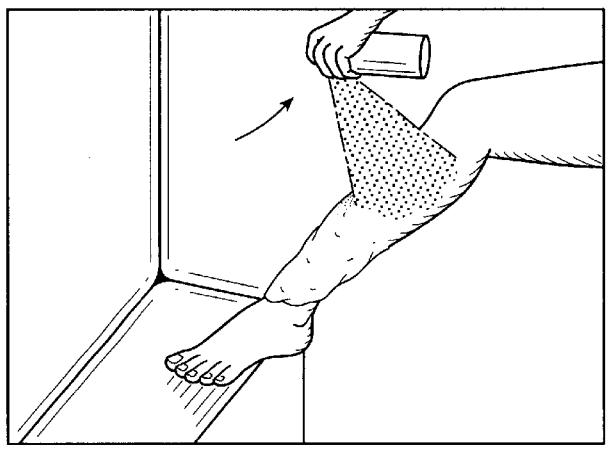
Figure 1:
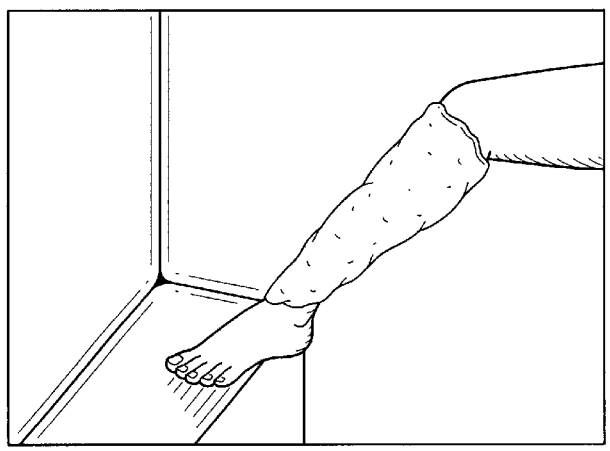

The invention features a method of shaving hair from an area of mammalian skin (preferably human skin) on which hair is growing. The method comprises spraying a shaving preparation directly onto the area of skin to form a dispersed layer of the shaving preparation on the area of skin without the need for hand spreading, and shaving the area of skin with a razor. Preferably, the shaving preparation is formulated to form a lather or foam upon contact with the skin. Since the shaving preparation is applied directly to the area of skin, the method of the present invention is especially useful for shaving large skin areas, such as the legs, because the shaving preparation may be quickly sprayed over a wide area. It is also convenient for shaving areas on the axilla or torso.

The invention also embraces a dispensing apparatus for spraying a shaving preparation directly onto an area of skin to be shaved. The dispensing apparatus comprises: (a) a container having an internal storage compartment; (b) a shaving preparation stored within the storage compartment; (c) a spray actuator (also known as a spray nozzle) in fluid communication with the storage compartment; and (d) propelling structure adapted to propel the shaving preparation from the storage compartment through the spray actuator. During use, the dispensing apparatus is typically held such that the spray actuator is about 7 cm to about 30 cm, preferably about 10 cm to about 25 cm, from the skin surface and sprays the shaving preparation in the form of droplets to form a dispersed layer of the shaving preparation on the area of skin without the need for hand spreading. The dispensing apparatus may be a pump spray or, preferably, an aerosol device in which the product is contained under pressure.

The dispensing apparatus will include a spray actuator that is preferably adapted to disperse the shaving preparation over an area having a width, measured at the widest point, of about 3 cm to about 25 cm, more preferably about 5 cm to about 20 cm, when the spray actuator is held a distance of about 15 cm from the area of skin being sprayed. Typically, useful sprays will cover an area of skin (i.e., the area where about 80% of the preparation is deposited) ranging from about 10 cm$^2$ to about 120 cm$^2$, preferably from about 20 cm$^2$ to about 70 cm$^2$, when the spraying is conducted for one second at a distance of 15 cm from the skin. Preferably, the spray actuator will be configured to disperse the shaving preparation in approximately a cone-shaped or a fan-shaped pattern, with a cone angle or fan angle of 10° to 90°, preferably 25° to 75°. The spray actuator will also preferably be configured to disperse the shaving preparation as droplets having a Sauter mean diameter between about 10 µm and about 200 µm, preferably between about 60 µm and about 130 µm. The Sauter mean diameter is the diameter of a droplet whose surface to volume ratio matches that of the entire spray. This measurement is described in Example 1. It has been found that spray actuators having an orifice area ranging from about $4\times10^{-4}$ cm$^2$ to about $20\times10^{-4}$ cm$^2$ can produce useful sprays. The dispensing apparatus will ideally spray the shaving preparation at a rate of less than about 3 grams/second, preferably at a rate of less than about 1 gram/second.

The shaving preparation is formulated such that its viscosity is suitable for forming a spray upon actuation of the dispensing apparatus. The viscosity of the composition influences the ability of the system to generate a spray. The preferred viscosity is very close to that of water at 1 centiPoise (cP), although viscosities in the range of 1–100 cP, more preferably –10 cP, may be used as well. The shaving preparation is also preferably formulated to produce a rich lather when dispensed from the dispensing apparatus directly onto the surface of an area of skin to be shaved. Following application to the skin, it should soften and support the hair prior to cutting, and lubricate and protect the skin from the passage of a razor over the skin. It also should provide the ability to keep track of areas that remain to be shaved.

In its most basic form, a shaving preparation within the scope of the present invention will be a solution, emulsion, or dispersion containing water and a surface-active agent. Advantageously, other cosmetic ingredients may be added to improve the application aesthetics and/or achieve other shave or skin benefits. For example, the shaving preparation may include one or more of the following components: beard wetting agents, skin conditioning agents, cleansing agents, lathering agents, foaming agents, emollients, humectants, soaps, detergents, surfactants, thickening agents, propellants/blowing agents, fragrances, colorants, preservatives, etc.

Typically, the shaving preparation will comprise, by weight, about 60 to 95%, preferably about 75 to 90%, water and about 1 to 25%, preferably about 3 to 20%, of a surface-active agent. The surface-active agent may include one or more water-soluble or water-dispersible soaps (including interrupted soaps), detergents, anionic surfactants, non-ionic surfactants, and/or amphoteric surfactants.

Water-soluble/-dispersible soaps include, for example, the sodium, potassium, and lower alkanolamine (preferably triethanolamine) salts of C10 to $C_{20}$, preferably $C_{12}$ to $C_{15}$, fatty acids. Typical fatty acids include lauric, oleic, coconut oil, myristic, palmitic, and stearic acid, and mixtures thereof. For purposes of the present invention, the aqueous soaps are also intended to include the interrupted soaps such as the sodium, potassium and lower alkanolamine (preferably triethanolamine) salts of N-fatty acyl sarcosines, wherein the fatty acyl moiety has 10 to 20, preferably 12 to 18, carbon atoms. Typical sarcosines include stearoyl sarcosine, myristoyl sarcosine, palmitoyl sarcosine, oleoyl sarcosine, lauroyl sarcosine, cocoyl sarcosine, and mixtures thereof The soaps (including the interrupted soaps) may be utilized in pre-neutralized form (i.e. as the sodium, potassium, or alkanolamine salt) or in the free acid form followed by subsequent neutralization with sodium hydroxide, potassium hydroxide and/or alkanolamine (preferably triethanolamine). In any event, the composition must contain sufficient base to neutralize or partially neutralize the soap component and adjust the pH to the desired level.

The aqueous surface-active agent may also include a non-ionic surfactant to improve lather quality, wettability, and/or rinsability. Suitable non-ionic surfactants will generally be included in an amount up to about 8%, preferably about 1 to 6%, of the composition. Preferred non-ionic surfactants include the polyoxyethylene ethers of fatty alcohols, acids, and amides, particularly those having 10 to 20, preferably 12 to 18, carbon atoms in the fatty moiety and about 8 to 60, preferably 10 to 30, ethylene oxide units. These include, for example, Oleth-20, Steareth-21, Ceteth-20, and Laureth-23. Other non-ionic surfactants include the polyoxyethylene ethers of alkyl substituted phenols, such as Nonoxynol-4 and Nonoxynol-20, fatty alkanolamides such as Lauramide DEA and Cocamide MEA, polyethoxylated sorbitan esters of fatty acids, such as Polysorbate-20, lauryl polyglucoside, sucrose laurate, and polyglycerol 8-oleate.

The aqueous surface-active agent may also include one or more anionic surfactants. These include, for example, the sodium, potassium, ammonium and substituted ammonium salts (such as the mono-, di- and triethanolamine salts) of $C_8$–$C_{22}$, preferably $C_{12}$–$C_{18}$, alkyl sulfates (e.g. sodium lauryl sulfate, ammonium lauryl sulfate), alkyl sulfonates (e.g. ammonium lauryl sulfonate), alkylbenzene sulfonates (e.g. ammonium xylene sulfonate), acyl isethionates (e.g. sodium cocoyl isethionate), acyl lactylates (e.g. sodium cocoyl lactylate) and alkyl ether sulfates (e.g. ammonium laureth sulfate).

The aqueous surface-active agent may also include one or more amphoteric surfactants. Suitable amphoteric surfactants include, for example, the betaines and sultaines such as cocoamidopropyl betaine, coco dimethyl carboxymethyl betaine, coco sultaine and the like.

In addition to the surface-active agent, the shaving preparation may optionally include a variety of other well-known cosmetic ingredients generally known for use in shaving preparations to improve the aesthetics and performance characteristics of the composition. Generally, the shaving preparation will be formulated so that it will have both good application aesthetics and good shaving characteristics.

The shaving preparation may contain a non-volatile paraffinic hydrocarbon fluid, typically in an amount of about 1 to 10% by weight of the composition. The terms "non-volatile" and "fluid" mean that these materials are liquid at room temperature and have a boiling point above 200° C. Such hydrocarbon fluids include mineral oils and branched-chain aliphatic liquids. These fluids typically have from about 16 to about 48, preferably about 20 to about 40, carbon atoms and a kinematic viscosity of about 5 to about 100 centiStokes (cSt), preferably about 10 to about 50 cSt, at 40° C. A preferred non-volatile paraffinic hydrocarbon fluid is selected from mineral oil with a kinematic viscosity of about 10 to about 50 cSt at 40° C., hydrogenated polyisobutene with a molecular weight of about 320 to about 420, and mixtures thereof.

It may also be desirable to include low concentrations of a water-soluble thickening agent in the shaving preparation to improve its consistency and stability, as well as to adjust its viscosity. These may include, for example, hydroxyalkyl cellulose polymers such as hydroxyethyl cellulose and hydroxypropyl cellulose (sold under the trademarks "Natrosol" and "Klucel", respectively), copolymers of acrylic acid and polyallyl sucrose (sold under the trademark "Carbopol"), carboxymethyl cellulose, cellulose methyl ether (sold under the trademark "Methocel"), and activated clays. The thickening agent is typically included in an amount of about 0.01 to 2%, preferably about 0.1 to 1%, by weight of the composition.

The shaving preparation may also include a fatty alcohol having 10 to 20, preferably 12 to 18, carbon atoms such as myristyl, lauryl and stearyl alcohol and octyl dodecanol. The fatty alcohol is typically included in an amount of up to 8%, preferably about 2 to 6%, by weight.

For shaving preparations that do not produce enough visual contrast between areas of the skin that have and have not been shaved, opacifiers may be added to the shaving preparation. Opacifiers may be either inorganic or organic compounds. Inorganic opacifiers include, for example, titanium dioxide, zinc oxide, talc, mica or coated mica (with oxides of titanium, tin, or iron or bismuth oxychloride), magnesium aluminum silicate, bismuth oxychloride, or other minerals. These compounds can be added as powders, dispersions, or complexes. Organic opacifiers include, for example, opaque emulsions (e.g., containing Styrene/PVP copolymer, vinyl polymers, or latexes), metal salts of amines containing 14–20 carbon atoms per molecule, alkanolamides containing 14–20 carbon atoms per molecule, organic alcohols containing 14–20 carbon atoms per molecule, insoluble salts of stearic acid, glycol mono- or distearates, propylene glycol and glycerol monostearates and palmitates. Combinations of these opacifiers can also be used. The opacifying additive is typically included in an amount of about 1 to 6%, preferably about 2 to 5%, by weight of the composition.

Humectants, emollients, lubricants, skin freshening/soothing agents and other additives may be utilized in the shaving preparation, provided that the final preparation is capable of forming a spray. Humectants include glycerin, sorbitol, liquid water-soluble polyols, propylene glycol, polyethylene glycol, ethoxylated/propoxylated ethers of methyl glucose, and ethoxylated/propoxylated ethers of lanolin alcohol. Emollients include fatty esters such as isopropyl myristate, decyl oleate, 2-ethylhexyl palmitate, PEG-7 glyceryl cocoate, and glyceryl linoleate, propoxylated fatty ethers such as PPG-10 cetyl ether and PPG-11 stearyl ether, di-and triglycerides such as lecithin and caprylic/capric triglyceride. Lubricants include polyethylene oxide and polyvinyl pyrrolidone. Skin freshening and soothing agents include menthol, aloe, aloe vera gel, allantoin, lanolin and oil-soluble lanolin derivatives, collagen and hyaluronic acid, fluotosurfactants, silicones (e.g. dimethicone, dimethiconol, dimethicone copolyol, stearyl dimethicone, cetyl dimethicone copolyol, phenyl dimethicone, cyclomethicone, etc.), vitamins (including vitamin precursors and derivatives) such as panthenol, vitamin E, tocopherol acetate, vitamin A palmitate, petrolatum, mineral oil, beeswax, saturated and unsaturated alcohols, hydrocarbons, various animal and vegetable oils, sodium pyrrolidone carboxylic acid, lactic acid, urea, L-proline, guanidine, pyrrolidone, water-soluble hexadecyl, myristyl, isodecyl or isopropyl esters of adipic, lactic, oleic, stearic, isostearic, myristic or linoleic acids and many of their alcohol esters, hydrolyzed protein and other collagen-derived proteins, and acetamide MEA. Other additives include colorants, fragrances, antioxidants, and preservatives.

Volatile components can be added to the shaving preparation to perform two functions: (1) to propel the shaving composition from its container (hence, these components are referred to as propellants) and (2) to cause the shaving preparation to foam (hence, these components are referred to as blowing agents or foaming agents). In the remainder of this text, we will refer to dual-role propellants/blowing agents simply as propellants. Propellants include compressed air, nitrous oxide, and carbon dioxide and, more typically, a volatile hydrocarbon or mixture of volatile hydrocarbons (typically with 3 to 6 carbon atoms) having a vapor pressure of 15 to 80 psig, preferably 30 to 70 psig, at about 20° C. The term volatile hydrocarbons is also intended to include the halohydrocarbons. A preferred propellant has the industry designation A-46 and is a mixture of isobutane and propane with a vapor pressure of 46 psig at about 20° C. Another preferred propellant has the industry designation A-31 and is isobutane with a vapor pressure of 31 psig at about 20° C. Other suitable propellants include propellant 152A (1,1-difluoroethane) and propellant A-70 (a mixture of propane and isobutane). When the propellant is a volatile hydrocarbon, it typically comprises about 1 to 8%, preferably about 2 to 5% by weight, of the composition.

Blowing (or foaming) agents can also be added to the formulation that cause the formulation to foam, but do not supply the major mechanical energy to propel the shaving composition from its container. Typical blowing agents include the volatile hydrocarbons or mixture of volatile hydrocarbons (typically with 3 to 6 carbon atoms) as described above. Components can also be added that generate volatile compounds (for example, $CO_2$ via chemical reaction), that, in turn, cause the formulation to foam.

A rich lather is characterized as having a stiffness, density, and durability such that it evenly covers the skin with a smooth, soft, adhesive coating that holds its bubble structure and shape for the shaving process. A good shaving lather will have a density, after dispensing, ranging between about 0.05 $g/cm^3$ to about 0.25 $g/cm^3$.

In practicing the method of the present invention, the shaving preparation is preferably dispensed from a dispensing apparatus comprising: (a) a container having an internal storage compartment; (b) a shaving preparation stored within the storage compartment; (c) a spray actuator (also known as a spray nozzle) in fluid communication with the storage compartment; and (d) propelling structure adapted to propel the shaving preparation from the storage compartment through the spray actuator. During use, the dispensing apparatus sprays the shaving preparation in the form of droplets to form a dispersed layer of the shaving preparation on the area of skin without the need for hand spreading. The dispensing apparatus may be a manually activated pump spray or, preferably, an aerosol device in which the product is contained under pressure.

Manually activated pump sprays typically include a squeeze trigger or finger-type pumping device as part of the propelling structure. Such pumping devices are well known in the art and typically include a pump chamber, an injection pipe member connected to a vertical pipe portion (piston), a cylinder, and a discharge valve, which communicates with the spray actuator. Fluid is sprayed from the pumping device under pumping pressure generated by the pumping action of an injection pipe member lifted and lowered vertically in a cylinder by an operating mechanism. The injection pipe member includes a vertical pipe portion, corresponding to a piston, which is forced into the cylinder. The fluid pressurized in the pump chamber exerts pressure, through means of a fluid passage in the injection pipe member, onto and through a flexible discharge valve, thereby causing the fluid to be sprayed from the spray actuator. A wide variety of manually activated pump spray dispensers may be used, including, for example, the dispensers described in US Pat. Nos. 4,082,223, 4,161,288, 4,558,821, 4,434,917, and 5,922,333, each of which is incorporated herein by reference. A preferred pump dispenser comprises a squeeze trigger for ease of application.

Other suitable dispensers may include as the propelling structure: (1) mechanically pressurized bag-in-sleeve systems in which a thin-walled inner bag containing the product is surrounded by an outer elastic sleeve that is expanded during the product filling process and provides dispensing power to expel the product (e.g., the ATMOS System available commercially from the Exxel Container Co.); (2) manually activated air pump spray devices in which a pump system is integrated into the container to allow the user to pressurize the container with air in order to expel the product (e.g., the "AIRSPRAY" system available from Airspray International); (3) piston barrier systems in which the product is separated from the driving means by a tight-fitting piston which seals to the side of the container and may be driven by a spring under tension, by a vacuum on the product side of the piston, by finger pressure, by gas pressure to the piston, or by a variety of other means known to the packaging industry; and (4) bag-in-can (SEPRO) systems in which the product is contained in a flexible bag within a can, with a suitable propellant injected into the space between the can and the flexible bag.

In the case of aerosol shaving preparations, the dispenser should be designed to hold the shaving preparation under pressure. Examples of dispensers capable of performing this function include standard tin-plate containers, aluminum-type containers, and glass or plastic bottles. Also suitable are bag-in-can containers such as SEPRO containers, described above.

An aerosol dispenser will typically also include a valve-actuator system. The valve portion of a valve-actuator system seals the shaving preparation within the container and, when actuated by operation of the actuator portion, allows the shave preparation to exit through the spray actuator, which has been previously described. The valve should also allow the composition to be dispensed preferably in all spatial orientations to facilitate direct skin application.

The invention will now be described further by way of the following examples.

EXAMPLES

The following examples illustrate representative spray shaving preparations suitable for direct application to skin. Examples 1–21 describe aerosol foams, while Examples 22–24 describe non-aerosol shaving preparations. All amounts are in weight percent unless otherwise noted. The names for all ingredients are INCI names unless otherwise noted.

Example 1

Example 1 illustrates the preparation of an aerosol spray shaving foam having the following formulation:

TABLE 1

| Ingredient | Amount (%) |
| --- | --- |
| Water | 88.25 |
| Stearic Acid | 4.18 |
| Laureth-23 | 1.38 |
| Sodium Lauryl Sulfate | 0.52 |
| Triethanolamine (99%) | 2.16 |
| BHT | 0.01 |
| Fragrance | 0.50 |
| Aeron A-31 Propellant | 3.00 |

The water was heated to 80–85° C., after which stearic acid was added. Once the stearic acid had melted, the laureth-23 was added, melted, and mixed well. Next, triethanolamine was added and the resulting composition mixed well for about 30 minutes to form a soap. The resulting soap was cooled to about 65° C., after which sodium lauryl sulfate was added and the composition mixed well. Next, the BHT was added, followed by mixing. The resulting composition was then cooled to room temperature and the fragrance added. The product was packaged with the Aeron A-31 propellant in an aerosol can using conventional techniques and mechanically shaken for 5 minutes.

The can was a standard aerosol can provided with a valve-actuator system that included an upright-inverted valve (Summit UI-3, available from Summit Packaging Systems, Inc.) and a two-piece mechanical break-up actuator (No. 77902 with insert 70151-2402, also available from Summit). The specification for this valve is Stem 1×0.018, meaning that the valve stem has a single opening measuring 0.018 inch (0.046 cm). This actuator incorporated a simplex geometry, otherwise known as a "pressure-swirl" geometry. This geometry includes an upstream swirl chamber in which a liquid stream is ported in such a way that an azimuthal swirling is imparted. The swirling produces a central air core in the orifice, causing the liquid to exit in the form of a thin, annular sheet of liquid that spreads out into a conical shape. The thinness of the liquid sheet accelerates the break-up of the sheet into droplets and leads to the formation of relatively small droplets that convert immediately into foam.

The spray device produced a cone-shaped spray that deposited onto the skin as a layer of rich lather that quickly covered a wide area of skin. The spray foam could be dispensed in all spatial orientations, thereby allowing easy and direct application. The deposited foam had sufficient viscosity, density, and quality to remain in place for the duration of the shave. It gave a comfortable, close shave and rinsed well.

The cone-shaped spray had a base cone diameter of about 9 cm at a distance of about 15 cm from the actuator. This corresponded to an area of coverage of about 28 cm$^2$. The droplet size of the spray had a Sauter mean diameter of 97 $\mu$m, with a range of 64 to 203 $\mu$m. The foam density was 0.07 to 0.25 g/ml.

The Sauter mean diameter is the diameter of a droplet whose surface to volume ratio matches that of the entire spray. The size range is defined such that 10% of the droplets by volume are smaller than the lower end of the range, and 10% of the droplets by volume are larger than the upper end of the range.

The droplet size distribution of the spray was characterized with a laser diffraction instrument (Malvern Spraytec RTS 5000 Real-Time Liquid Droplet Sizer). The instrument measures the scattered light intensity caused by the drops as they pass through the analyzer's laser beam. A lens focuses the scattered light onto a series of semicircular photodiodes. Each photodiode is positioned to be most sensitive to a particular small range of drop sizes. The instrument used had a drop size range of 1400 $\mu$m. Interpretation of the measured light energy distribution as a drop size distribution is performed by the manufacturer's software.

The distance between the actuator and laser beam was about 10 cm. The actuator and the laser beam were about the same height, and the actuator's centerline was perpendicular to the laser beam. The spray foam can was between full and two-thirds full, and was actuated in an upright position for about one-half of a second. The Malvern instrument was operated in Flash Mode with light intensity readings collected over 5 seconds, 100 sets of readings collected per second, and acquisition triggered on a 2% decrease in transmission.

Example 2

The procedure of Example 1 was followed except that the aerosol can was a SEPRO type bag-in-can container equipped with a Summit valve #003-972-009. The shaving formulation was gassed with 2.5% Aeron A-31 propellant and the bag was pressurized (bottom gassed) with Aeron A-46 propellant. (In this case, the Aeron A-46 is not serving as a blowing agent.) The product dispensed as a cone-shaped spray that deposited onto the skin as a layer of rich lather that quickly covered a wide area of skin similar in size to that described in Example 1. The deposited foam had sufficient viscosity, density, and quality to remain in place for the duration of the shave. It gave a comfortable, close shave and rinsed well. Laser diffraction analysis (performed according to the procedure described in Example 1) indicated that the droplets in the spray had a Sauter mean diameter of 101 μm, with a range of 61–184 μm.

Example 3

The procedure of Example 1 was followed except that the aerosol valve was a Summit valve #003-972-068 valve. The specification for this valve is stem 2×0.018, meaning that the valve stem has two openings, each measuring 0.018 inch (0.046 cm). The product dispensed as a cone-shaped spray that deposited onto the skin as a layer of rich lather that quickly covered a wide area of skin similar in size to that described in Example 1.

Examples 4–8

The procedure of Example 1 was followed except that the actuator was replaced with an actuator set forth in Table 2. All of these actuators are commercially available. In each case, the product dispensed as a cone-shaped spray that deposited onto the skin as a layer of rich lather that quickly covered a wide area of skin. In each case, the area of coverage ranged from about 20 to 130 $cm^2$ with the actuator 15 cm from the surface of the skin. The spray foam could be dispensed in all spatial orientations, thereby allowing easy and direct application. The deposited foam had sufficient viscosity, density, and quality to remain in place for the duration of the shave. In each case, the product gave a comfortable, close shave and rinsed well.

TABLE 2

| EXAMPLE | ACTUATOR | ORIFICE DIAMETER (INCHES) [CM] |
|---|---|---|
| 4 | Summit 77931 (with Insert 70046-2402) | 0.013 [0.033] |
| 5 | Summit 77902 (with Insert 70150-2402) | 0.016 [0.041] |
| 6 | Summit 77902 (with Insert 70188-2402) | 0.020 [0.051] |
| 7 | Seaquist* 2204-06490-18 | 0.018 [0.041] |
| 8 | Seaquist* 2204-06490-16 | 0.016 [0.041] |

*Seaquist Perfect Dispensing, Inc.

Examples 9–12

The procedure of Example 1 was followed except that the propellant was replaced with a different propellant. The formulations are set forth in Table 3. Each of these agents is commercially available and represents a single hydrocarbon or hydrocarbon mixture.

TABLE 3

| Ingredient | Example 9 | Example 10 | Example 11 | Example 12 |
|---|---|---|---|---|
| Water | 86.25 | 88.25 | 88.25 | 87.25 |
| Stearic Acid | 4.18 | 4.18 | 4.18 | 4.18 |
| Laureth-23 | 1.38 | 1.38 | 1.38 | 1.38 |
| Triethanol Amine | 2.16 | 2.16 | 2.16 | 2.16 |
| Sodium Lauryl Sulfate | 0.52 | 0.52 | 0.52 | 0.52 |
| BHT | 0.01 | 0.01 | 0.01 | 0.01 |
| Fragrance | 0.50 | 0.50 | 0.50 | 0.50 |
| Aeron A-17 | 5.00 | 0.00 | 0.00 | 0.00 |
| Aeron A-24 | 0.00 | 3.00 | 0.00 | 0.00 |
| Aeron A-46 | 0.00 | 0.00 | 3.00 | 0.00 |
| Aeron A-31 | 0.00 | 0.00 | 0.00 | 4.00 |

In each case, the product dispensed as a cone-shaped spray that deposited onto the skin as a layer of rich lather that quickly covered a wide area of skin. The spray foam could be dispensed in all spatial orientations, thereby allowing easy and direct application. The deposited foam had sufficient viscosity, density, and quality to remain in place for the duration of the shave. In each case, the product gave a comfortable, close shave and rinsed well.

Examples 13–16

The procedure of Example 1 was followed except that the formulation was replaced with a different formulation as set forth in Table 4.

TABLE 4

| Ingredient | Example 13 | Example 14 | Example 15 | Example 16 |
|---|---|---|---|---|
| Water | 84.12 | 86.60 | 89.43 | 90.31 |
| Stearic Acid | 6.27 | 5.02 | 3.58 | 3.14 |
| Laureth-23 | 2.07 | 1.66 | 1.19 | 1.04 |
| Triethanol Amine | 3.23 | 2.59 | 1.85 | 1.62 |
| Sodium Lauryl Sulfate | 0.78 | 0.63 | 0.45 | 0.39 |
| BHT | 0.02 | 0.02 | 0.01 | 0.01 |
| Fragrance | 0.50 | 0.50 | 0.50 | 0.50 |
| Aeron A-31 | 3.00 | 3.00 | 3.00 | 3.00 |

In each case, the product dispensed as a cone-shaped spray that deposited onto the skin as a layer of rich lather that quickly covered a wide area of skin. The spray foam could be dispensed in all spatial orientations, thereby allowing easy and direct application. The deposited foam had sufficient viscosity, density, and quality to remain in place for the duration of the shave. In each case, the product gave a comfortable, close shave and rinsed well.

Example 17

The procedure of Example 1 was followed except that the formulation was replaced with the formulation set forth in Table 5.

TABLE 5

| Ingredient | Amount (%) |
|---|---|
| Water | 91.32 |
| Palmitic Acid | 2.12 |
| Laureth-23 | 0.93 |
| Triethanolamine (99%) | 1.13 |
| Cetyl Dimethicone Copolyol | 0.19 |

TABLE 5-continued

| Ingredient | Amount (%) |
| --- | --- |
| Mineral Oil | 0.31 |
| Stearyl Alcohol | 0.31 |
| Lauramide DEA | 0.15 |
| PEG-150 Distearate | 0.05 |
| Imidazolidinyl Urea | 0.0016 |
| Methylparaben | 0.0005 |
| Propylparaben | 0.00003 |
| Freeze Dried Aloe Powder | 0.0015 |
| Fragrance | 0.50 |
| Aeron A-31 Propellant | 3.00 |

The aqueous phase was prepared as follows. The water was heated to 80° C., after which palmitic acid was added. Once the palmitic acid had melted, the laureth-23 was added, melted, and mixed well. Next, triethanolamine was added and the resulting composition mixed well for about 15 minutes to form a soap.

Stearyl alcohol, mineral oil, lauramide DEA, cetyl dimethicone copolyol, PEG-150 distearate, and BHT were mixed and heated at 55° C. to form the oil phase. The oil phase was combined with the aqueous phase at 80° C. and mixed well for about 15 minutes. The resulting mixture was then cooled to room temperature and the imidazolidinyl urea, methylparaben, and propylparaben added, and then mixed well. Next, the fragrance was added, followed by gentle mixing. The aloe was then dissolved in make-up water and added with slow mixing to form the product formulation which was then packaged in an aerosol can as described in Example 1.

The product dispensed as a cone-shaped spray that deposited onto the skin as a layer of rich lather that quickly covered a wide area of skin. The spray foam could be dispensed in all spatial orientations, thereby allowing easy and direct application. The deposited foam gave a comfortable, close shave and rinsed well.

Example 18

The procedure of Example 1 was followed except that the formulation was replaced with the formulation set forth in Table 6.

TABLE 6

| Ingredient | Amount (%) |
| --- | --- |
| Water | 88.17 |
| Glycereth-26 | 0.64 |
| Palmitic Acid | 2.73 |
| Triethanolamine (99%) | 1.67 |
| Hydrogenated Polyisobutene | 0.64 |
| Oleth-20 | 1.77 |
| Lauramide DEA | 0.48 |
| PEG-150 Distearate | 0.08 |
| Zonyl FSK-1%* | 0.32 |
| Aloe Vera Dried Powder | 0.0016 |
| Fragrance | 0.50 |
| Aeron A-31 Blowing Agent | 3.00 |

* = Tradename for polytetrafluoroethylene acetoxypropyl betaine (Dupont)

The aqueous phase was prepared as follows. Glycereth-26 was dissolved in the water and the resulting mixture heated to 80–85° C., after which palmitic acid and hydrogenated polyisobutene were added. Once the palmitic acid and hydrogenated polyisobutene had melted, the triethanolamine was added and mixed well for about 15 minutes to form a soap.

Oleth-20, Lauramide DEA, and PEG-150 distearate were mixed and heated at 55° C. to form the oil phase. The oil phase was combined with the aqueous phase at 80° C. and mixed well for about 15 minutes. The resulting mixture was then cooled to room temperature and the Zonyl FSK added and then mixed well. Next, the fragrance was added, followed by gentle mixing. The aloe was then dissolved in make-up water and added with slow mixing to form the product formulation which was then packaged in an aerosol can as described in Example 1.

The product dispensed as a cone-shaped spray that deposited onto the skin as a layer of rich lather that quickly covered a wide area of skin. The spray foam could be dispensed in all spatial orientations, thereby allowing easy and direct application. The deposited foam gave a comfortable, close shave and rinsed well.

Example 19

The procedure of Example 1 was followed except that the formulation was replaced with the soap-free formulation set forth in Table 7.

TABLE 7

| Ingredient | Amount (%) |
| --- | --- |
| Ethanol | 6.00 |
| Ethyl Ester of PVM/MA Copolymer | 4.00 |
| Dimethicone Copolyol | 0.10 |
| Water | 81.07 |
| PVP/VA Copolymer | 1.00 |
| Sodium Lauryl Sulfate | 1.00 |
| Oleth-20 | 0.50 |
| Cocamide MEA | 0.05 |
| Methyl Paraben | 0.10 |
| Aminomethyl Propanol | 0.53 |
| Stearalkonium Chloride | 0.05 |
| Steareth-16 | 0.10 |
| Panthenol | 0.50 |
| Fragrance | 0.50 |
| Aeron A-46 | 5.00 |

The alcohol phase was prepared by dissolving ethyl ester of PVM/MA copolymer in ethanol, after which dimethicone was added and mixed well. The aqueous phase was prepared by heating the water to 65° C., after which the PVP/VA copolymer was added and mixed well. The oil phase was prepared by mixing the oleth-20, cocamide MEA, and steareth-16 at 60° C. to form a blend. The oil phase was then added to the aqueous phase at 65° C. and mixed well. Next, the methylparaben was added to the mixture, followed by mixing, after which the aminomethyl propanol, stearalkonium chloride, and panthenol were added and mixed until uniform. The resulting composition was cooled to room temperature, after which the alcohol phase was added and mixed well. The fragrance was then added and mixed gently to form the product. The product was then packaged in an aerosol can as described in Example 1.

The product dispensed as a cone-shaped spray that deposited onto the skin as a layer of rich lather that quickly covered a wide area of skin. The spray foam could be dispensed in all spatial orientations, thereby allowing easy and direct application. The deposited foam gave a comfortable, close shave and rinsed well.

Example 20

The procedure of Example 1 was followed except that the formulation was replaced with the soap-free formulation set forth in Table 8.

TABLE 8

| Ingredient | Amount (%) |
| --- | --- |
| Water | 77.16 |
| PVP/VA Copolymer | 1.04 |
| Polyquaternium-10 | 0.10 |
| Sodium Lauryl Sulfate | 0.46 |
| Sodium Lauroyl Sarcosinate | 0.97 |
| Polysorbate-20 | 13.03 |
| Sorbitan laurate | 0.87 |
| Ceteth-20 | 2.90 |
| Fragrance | 0.50 |
| Aeron A-46 | 3.00 |

Phase A was prepared by mixing the ceteth-20 and the polysorbate-20 at 60° C. to form a blend. The main batch was prepared by dispersing the polyquaternium-10 in water and mixing until the polymer hydrated completely, followed by heating at 60° C. The PVP/VA copolymer was then added and mixed well. Next, Phase A was added to the main batch at 60° C. and mixed well for about 20 minutes. The sodium lauryl sulfate, sodium lauroyl sarcosinate, and sorbitan laurate were then added to the mixture, followed by mixing until a uniform composition formed. The composition was cooled to room temperature, after which the fragrance was added, followed by gentle mixing. The product was then packaged in an aerosol can as described in Example 1.

The product dispensed as a cone-shaped spray that deposited onto the skin as a layer of rich lather that quickly covered a wide area of skin. The spray foam could be dispensed in all spatial orientations, thereby allowing easy and direct application. The deposited foam gave a comfortable, close shave and rinsed well.

Example 21

The procedure of Example 1 was followed except that the formulation was replaced with the soap-free formulation set forth in Table 9.

TABLE 9

| Ingredient | Amount (%) |
| --- | --- |
| Water | 87.54 |
| Polyquaternium-10 | 0.03 |
| Ceteth-20 | 0.96 |
| PEG-150 Distearate | 0.96 |
| Cocomidopropyl Betaine | 1.43 |
| Polysorbate-20 | 4.30 |
| Sorbitan Laurate | 0.29 |
| Fragrance | 0.50 |
| Aeron A-46 | 4.00 |

Phase A was prepared by mixing the ceteth-20 and the PEG-150 distearate at 60° C. to form a blend. The main batch was prepared by dispersing the polyquaternium-10 in water and mixing until the polymer hydrated completely, followed by heating at 60° C. Next, the cocomidopropyl betaine, the polysorbate-20, and sorbitan laurate were added, followed by addition of Phase A. The resulting composition was mixed until uniform and then cooled to room temperature. Next, the fragrance was added, followed by gentle mixing. The product was then packaged in an aerosol can as described in Example 1.

The product dispensed as a cone-shaped spray that deposited onto the skin as a layer of rich lather that quickly covered a wide area of skin. The spray foam could be dispensed in all spatial orientations, thereby allowing easy and direct application. The deposited foam gave a comfortable, close shave and rinsed well.

Example 22

Example 22 illustrates the preparation of a non-aerosol spray shaving foam having the formulation set forth in Table 10.

TABLE 10

| Ingredient | Amount (%) |
| --- | --- |
| Water | 90.35 |
| Ammonium Laureth Sulfate | 3.33 |
| Ammonium Lauryl Sulfate | 1.67 |
| Lauramide DEA | 1.09 |
| Palmitic Acid | 0.14 |
| Cocoamidopropyl Betaine | 0.14 |
| Sodium chloride | 2.00 |
| Citric Acid | 1.00 |
| Tetrasodium EDTA | 0.06 |
| Fragrance | 0.20 |
| Preservative | 0.03 |

Ammonium laureth sulfate, ammonium lauryl sulfate, lauramide DEA, palmitic acid, and cocoamidopropyl betaine were combined and heated to 55° C. The mixture was then stirred till homogeneous and then water was added. Next, tetrasodium EDTA was added with mixing. The solution was then cooled to 35° C., and the fragrance and preservative were added. The pH was adjusted, and the viscosity was decreased to <15 centiPoise with sodium chloride. The composition was then loaded into plastic bottles fitted with a typical trigger-type sprayer device (CALMAR Inc., Models Magnum 1300 or TS-800) and a finger-tip sprayer device (EMSAR Inc., #37MS Air Force II, Model 180 MCL, with Actuator A6 and Insert 1314).

The product dispensed as a cone-shaped spray that deposited onto the skin as a layer of thin lather that quickly covered a wide area of skin, thereby allowing easy and direct application.

Example 23

The procedure of Example 22 was followed except that the formulation was replaced with the formulation set forth in Table 11.

TABLE 11

| Ingredients | Amount (%) |
| --- | --- |
| Water | 94.41 |
| PEG-5M | 0.07 |
| Guar Hydroxypropyltirmonium Chloride | 0.17 |
| Citric Acid | 0.03 |
| Ammonium Lauryl Sulfate | 0.94 |
| Ammonium Laureth Sulfate | 1.89 |
| Cocoamidopropyl Betaine | 0.08 |
| Lauramide DEA | 0.62 |
| Palmitic Acid | 0.08 |
| PEG 150 Distearate | 0.08 |
| Sodium Citrate | 0.02 |
| Sodium Lauroyl Sarcosinate | 0.57 |
| PEG-7-Glyceryl Cocoate | 0.10 |
| Sodium Lauroyl Lactylate | 0.33 |
| Euperlan PK-771* | 0.33 |

TABLE 11-continued

| Ingredients | Amount (%) |
| --- | --- |
| Preservative | 0.01 |
| Tetrasodium EDTA | 0.04 |
| Fragrance | 0.23 |

*Mixture of glycoldistearate, sodium laureth sulfate, cocamide DEA, and laureth 10, manufactured by Henkel Corporation.

The polymeric phase was prepared by dispersing PEG-5M into a third of the water; next, the guar was added and mixed until completely dissolved. Next, the citric acid was added and the mixture blended to cause the guar to completely hydrate. The polymeric phase was then mixed with the remaining water until uniform. The ammonium lauryl sulfate, ammonium laureth sulfate, and cocamidopropyl betaine were added and the mixture heated to 65° C. The lauramide DEA and palmitic acid were then added under slow mixing conditions. The sodium lauroyl sarcosinate, PEG 150 distearate, sodium citrate, PEG-7 glyceryl cocoate and sodium lauroyl lactylate were added to the mixture and mixed well after each addition. The composition was cooled to room temperature, after which the Euperlan PK-771 fragrance, tetrasodium EDTA, and the preservative were added and mixed gently. The composition was loaded into plastic bottles fitted with trigger-type and finger-tip sprayer devices, as described in Example 22.

The product dispensed as a cone-shaped spray that deposited onto the skin as a layer of thin lather that quickly covered a wide area of skin, thereby allowing easy and direct application.

Example 24

A non-aerosol spray foam was prepared by taking the formulation in Example 20, minus the Aeron A-46 propellant, and loading it into the plastic bottles fitted with trigger-type and finger-tip sprayer devices, as described in Example 22.

The product dispensed as a cone-shaped spray that deposited onto the skin as a layer of thin lather that quickly covered a wide area of skin, thereby allowing easy and direct application.

Other embodiments are within the following claims.

What is claimed is:

1. A method of shaving hair from an area of skin located on the leg of a human, which method comprises spraying a shaving preparation comprising a foaming agent directly onto said area of skin to form a dispersed layer of said shaving preparation on said area of skin without the need for hand spreading, and shaving said area of skin with a razor.

2. The method of claim 1 wherein said area of skin is located on a leg.

3. The method of claim 1 wherein said area of skin is located on an axilla or a torso.

4. The method of claim 1 wherein said area of skin is human skin.

5. The method of claim 1 wherein said shaving preparation comprises water and a surface active agent.

6. The method of claim 5 wherein said surface active agent is selected from the group consisting of soap, interrupted soap, detergent, anionic surfactant, non-ionic surfactant, amphoteric surfactant, and combinations thereof.

7. The method of claim 6 wherein said shaving preparation is contained within a hand-held spray dispenser comprising an internal storage compartment that stores said shaving preparation; a spray actuator in fluid communication with said storage compartment; and propelling structure adapted to propel said shaving preparation from said storage compartment through said spray actuator.

8. The method of claim 7 wherein said spray actuator is held at a distance of about 7 cm to about 30 cm from said area of skin during said spraying of said shaving preparation.

9. The method of claim 7 wherein said spray actuator is held at a distance of about 10 cm to about 25 cm from said area of skin during said spraying of said shaving preparation.

10. The method of claim 7 wherein said spray actuator disperses the shaving preparation over an area having a width, measured at the widest point, of about 3 cm to about 25 cm when said spray actuator is held a distance of about 15 cm from said area of skin.

11. The method of claim 7 wherein said spray actuator disperses the shaving preparation over an area having a width, measured at the widest point, of about 5 cm to about 20 cm when said spray actuator is held a distance of about 15 cm from said area of skin.

12. The method of claim 7 wherein said spray actuator disperses the shaving preparation in approximately a cone-shaped or a fan-shaped pattern.

13. The method of claim 7 wherein said propelling structure comprises a manually activated pumping device.

14. The method of claim 13 wherein said pumping device comprises a finger-type pumping device.

15. The method of claim 13 wherein said pumping device comprises a squeeze trigger-type pumping device.

16. The method of claim 7 wherein said propelling structure is adapted to maintain said shaving preparation under pressure in said storage compartment.

17. The method of claim 16 wherein said propelling structure comprises a propellant included in said storage compartment with said shaving preparation.

18. The method of claim 16 wherein said propelling structure comprises a propellant external to said storage compartment that exerts pressure on said storage compartment.

19. The method of claims 13, 14, 15, 16, or 18 wherein said shaving preparation comprises a blowing agent.

20. The method of claim 7 wherein said dispersed layer forms a lather having a density ranging from about 0.05 g/cm$^3$ to about 0.20 g/cm$^3$.

21. The method of claim 7 wherein said spray actuator disperses the shaving preparation as droplets having a Sauter mean diameter between about 10 $\mu$m and about 200 $\mu$m.

22. The method of claim 7 wherein said spray actuator disperses the shaving preparation as droplets having a Sauter mean diameter between about 60 $\mu$m and about 130 $\mu$m.

23. The method of claim 7 wherein said shaving preparation is dispensed at a rate of less than about 3 grams/second.

24. The method of claim 7 wherein said shaving preparation is dispensed at a rate of less than about 1 gram/second.

25. A method of shaving hair from an area of skin located on the leg of a human, which method comprises spraying a shaving preparation comprising an opaciying agent directly onto said area of skin to form a dispersed layer of said shaving preparation on said area of skin without the need for hand spreading, and shaving said area of skin with a razor.

26. A method of shaving hair from an area of skin located on the leg of a human, which method comprises spraying a shaving preparation directly onto said area of skin to form a dispersed layer of said shaving preparation on said area of skin without the need for hand spreading, and shaving said area of skin with a razor;

27. The method of claim 26, wherein said surface active agent is selected from the group consisting of soap, interrupted soap, detergent, anionic surfactant, non-ionic surfactant, amphoteric surfactant, and combinations thereof.

28. The method of claim 26, wherein said propelling structure comprises a propellant included in said storage compartment with said shaving preparation.

29. The method of claim 26, wherein said dispersed layer forms a lather having a density ranging from about 0.05 g/cm3 to about 0.20 g/cm3.

30. The method of claim 26, wherein said spray actuator disperses said shaving preparation over an area of skin ranging from about 10 cm2 to about 120 cm2 when held a distance of about 15 cm from said area of skin and said spraying is conducted for about one second.

* * * * *